United States Patent [19]
Garbassi et al.

[11] Patent Number: 5,484,897
[45] Date of Patent: Jan. 16, 1996

[54] ORGANOMETALLIC COMPLEXES OF LANTHANIDES AND THEIR USE IN THE POLYMERIZATION OF UNSATURATED MONOMERS

[75] Inventors: Fabio Garbassi; Paolo Biagini, both of Novara; Piero Andreussi, Milan; Gabriele Lugli, San Donato Mil.se, all of Italy

[73] Assignee: Enichem Elastomeri S.r.l., Milan, Italy

[21] Appl. No.: 281,221

[22] Filed: Jul. 27, 1994

[30] Foreign Application Priority Data

Aug. 6, 1993 [IT] Italy .................. MI93A1793

[51] Int. Cl.$^6$ .................. C07F 5/00; B01J 23/00
[52] U.S. Cl. .................. 534/15
[58] Field of Search .................. 534/15; 502/302

[56] References Cited

U.S. PATENT DOCUMENTS

| | | | |
|---|---|---|---|
| 4,520,123 | 5/1985 | Hall | 502/153 |
| 4,603,185 | 7/1986 | Benton et al. | 526/161 |
| 5,153,157 | 10/1992 | Hlatky et al. | 502/117 |

OTHER PUBLICATIONS

Wu, et al., "CP/MAS $^{89}$Y NMR Spectroscopy: A Facile Method for Characterizing Yttrium–Containing", Inorg. Chem. vol. 32, pp. 1130–1134, 1993.

*Primary Examiner*—Shean Wu
*Attorney, Agent, or Firm*—Oblon, Spivak, McClelland, Maier & Neustadt

[57] ABSTRACT

Organometallic complexes of lanthanides with a well-defined stoichiometry which can be used in the stereospecific polymerization of unsaturated monomers, can be represented by the general formula:

$$Me(OR)_3 * (Me_1 R^1 R^2 R^3)_x$$

wherein, Me represents a metal with atomic number 21, 39, or an atomic number between 57 and 71, OR is an alkoxylic group of an alcohol; Me represents a metal of the group IIIA, whereas $R^1$, $R^2$, $R^3$ can be H, or a linear, branched or cyclo-aliphatic alkyl radical containing from 1 to 10 carbon atoms and x is an integer (3 or 4) and depends on the type of alkoxide used.

The preparation of the complexes is described and their use in the stereospecific polymerization of unsaturated monomers.

10 Claims, 2 Drawing Sheets

I.R. SPECTRUM OF Nd(OMe)$_3$(AlMe$_3$)$_4$, THIN PAYER

I.R. SPECTRUM IN NUJAL OF $Nd(OBu^t)_3(AlMe_3)_3$

ORGANOMETALLIC COMPLEXES OF LANTHANIDES AND THEIR USE IN THE POLYMERIZATION OF UNSATURATED MONOMERS

The present invention relates to new organometallic complexes of elements belonging to the group of lanthanides, their preparation and their use in the stereospecific polymerization of unsaturated monomers.

BACKGROUND OF THE INVENTION

It is known in the art that the salts of metals belonging to the group of lanthanides, together with alkyls of metals belonging to the main groups from 1 to 3 of the periodic table and in the presence of halogenating agents, can form active catalytic systems in the Ziegler-Natta type polymerization reaction of both olefinic and diolefinic unsaturated monomers.

The systems are among the most stereospecific and active for the 1,4-cis polymerization of butadiene and in addition the elastomer produced has better mechanical properties than those of the polybutadienes produced with other catalytic systems.

A vast collection of examples of ternary catalytic systems based on metal salts of the group of lanthanides is provided in the publication by G. Allen and J. Bevington "Comprehensive Polymer Science" Vol. 4, chapter 5 page 53, published by Pergamon Press in 1989.

Other particularly detailed references can be found in the articles appearing in the magazines Inorganica Chimica Acta, vol. 130 page 125 of 1987 and Polymer, vol. 29, page 1516 of 1988.

A metal belonging to the group of lanthanides refers, as is generally accepted in the known art, to a metal belonging to the group comprising: scandium, with atomic number 21, yttrium, having atomic number 39, and/or a metal having an atomic number between that of lanthanum (57) and that of lutetium (71); these metals belong to group IIIA of the periodic table, according to the IUPAC definition prior to 1985.

From the point of view of patents, valid examples of ternary catalytic systems based on lanthanides are represented by German patents DE 1.812.935, DE 2.833.721, DE 2.848.964 and DD 243.034.

In most of the above cases, the catalytic systems are prepared by mixing the three components directly in the presence of the unsaturated compound to be polymerized, a method known in the art as "in situ preparation of the catalytic mixture".

Another technique of the known art involves the preparation of the catalytic mixture in a suitable solvent (preformation) and then the resulting solution or suspension is put in contact with the solution of the unsaturated compound to be polymerized. In this latter case, the preformed mixture of the catalyst can be left to age for a fixed period before being put in contact with the unsaturated monomer to be polymerized.

In all of the above cases, the claimed mixtures form catalytic systems suitable for the polymerization of unsaturated monomers in general and in particular butadiene.

These catalytic mixtures, however, owing to their complexity, are not structurally defined and cannot be isolated as defined products, but must be used as such after the mixing of the components; it is not even possible to isolate the organometallic derivatives of the metals involved in the catalytic reaction.

On the other hand, apart from the advantage of having stoichiometrically well-defined products, especially when they are used as components of polymerization catalytic systems, it would also be useful for the reproducibility of the chemical-physical characteristics of the polymers produced. In other words, with catalysts deriving from well-defined products, polymers can be obtained having reproducible and constant molecular weights and molecular weight distribution.

Another advantage is that variations in the characteristics of the polymers can be programmed by varying the parameters relating to the catalytic component itself.

SUMMARY OF THE INVENTION

The Applicant has now found, and this forms the first aspect of the present invention, that solid or liquid compounds can be obtained by the reaction between an alcoholate of a metal of the lanthanide group and a trialkyl aluminium. These complexes are isolated as solid or liquid compounds with a well-defined stoichiometry, and are therefore univocally defined chemical compounds in every sense.

If these complexes are solid products, they can be crystallized, and analyzed with the conventional techniques of elementary analysis and also by x-ray diffraction, obtaining the basic parameters of the crystalline cell.

In accordance with what is specified above, a second aspect of the present invention relates to organometallic complexes of lanthanides which can be represented by the general formula, $$Me(OR)_3 * (Me_1 R^1 R^2 R^3)_x \qquad (I)$$

wherein:
Me represents a metal with atomic number 21, 39, or an atomic number between 57 and 71,
OR is an alkoxylic group wherein R represents a linear, branched or cyclo-aliphatic alkyl radical containing from 1 to 10 carbon atoms,
$Me_1$ represents a metal of the group IIIA, i.e. the group of metals containing Al, Ga and In, according to the IUPAC definition prior to the year 1985, whereas
$R^1, R^2, R^3$, can be independently H, or a linear, branched or cyclo-aliphatic alkyl radical containing from 1 to 10 carbon atoms and
x is an integer which is 3 or 4.

The value of X in the structural formula (I) is 3 for alkoxylic groups with a number of carbon atoms higher than 1, whereas it is 4 if —OR is —OCH$_3$.

The present invention also relates, and this is a further aspect of the invention, to a synthesis method for the preparation of the components having general formula (I) and the use of these complexes in the polymerization of olefinic and/or diolefinic monomers.

Complexes belonging to general formula (I) indicated above form a new chemical group, with a defined stoichiometry and can be characterized with the modern techniques of spectroscopic analysis as well as with the chemical analyses of the elements of which they consist.

DESCRIPTION OF THE PREFERRED EMBODIMENTS

Figure 1:
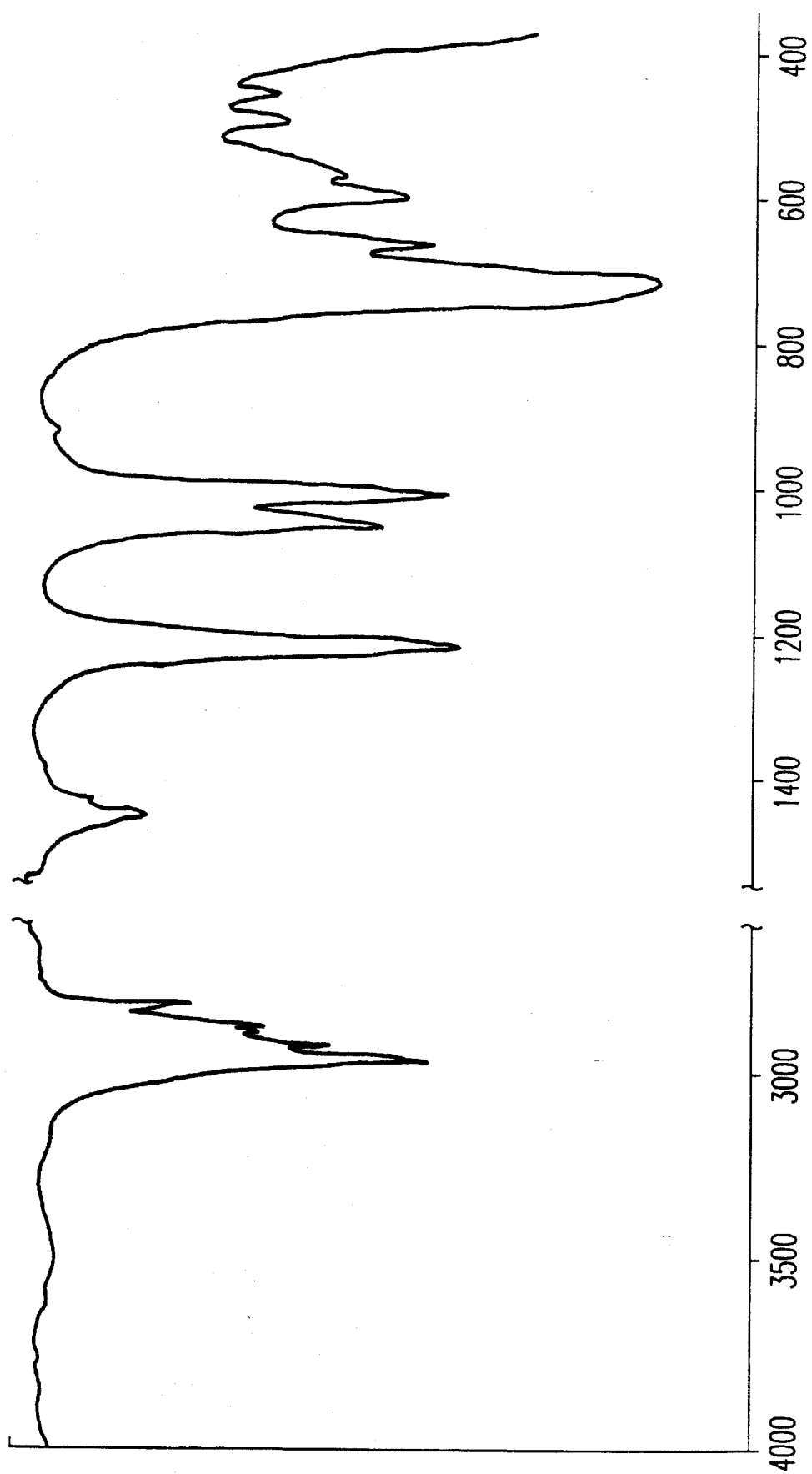
FIG. 1, I.R. Spectrum of Nd(OMe)$_3$(AlMe$_3$)$_4$.

A preferred aspect of the present invention relates to catalytic complexes having general formula (I), wherein Me is a neodymium (Nd), praseodymium (Pr) or yttrium (Y) atom respectively.

An equally preferred aspect of the present invention relates to catalytic complexes having general formula (I) wherein OR is an alkoxylic group wherein R represents a linear, branched or cyclo-aliphatic alkyl radical containing from 1 to 4 carbon atoms.

A further aspect of the present invention relates to catalytic complexes having general formula (I) wherein OR is an alkoxylic group wherein R represents a methyl group, propyl group, isopropyl group, n-butyl group or ter-butyl group respectively.

As already specified, the present invention also relates to a preparative method for the synthesis and separation of the compounds. The reaction is carried out by dissolving or suspending the alcoholate of the lanthanide Me(OR)$_3$ in a suitable solvent and adding a solution of aluminium trialkyl to this solution/suspension, in a molar ratio Al/Me of values of between 1–4, in the same solvent at a temperature of between −30° and +100° C. Temperatures of between 0° and +10° C. are preferred.

The solvent in which the reaction takes place does not require particular characteristics. Suitable solvents however can be all aliphatic, cyclo-aliphatic and aromatic hydrocarbons with preference for those which have the best solvent characteristics with respect to the substances to be reacted. Solvents with a weak base character, such as ethyl ether, can still be used but are not considered the best.

The addition of the solution of aluminium trialkyl requires from 30 to 90 minutes and is carried out continuously under inert gas because both the reagents used and the reaction products are sensitive to oxygen and humidity.

At the end of the addition of aluminium trialkyl a solution is obtained which is filtered to eliminate, if present, any traces of solid in suspension. The filtrate is then accurately liberated from the solvent or possible excess of aluminium trialkyl which has not reacted.

This operation is carried out under force vacuum (10$^{-3}$ Pa) and for a period of between 5 and 15 hours depending on the physical form of the end-product recovered. The final residue, solid or liquid, is used for the chemical analyses of the elements and necessary spectroscopic analyses.

Although the procedure described is generally valid, it is obvious that the physical state of the complex obtained after evaporation of the solvent depends on the type of lanthanide alcoholate and aluminium trialkyl and on their molar ratio.

For example, from the reaction between Nd(OBu$^n$)$_3$ and Al(CH$_3$)$_3$, Al(Bu$^i$)$_3$ or AlH(Bu$^i$)$_2$, viscous liquids are obtained whereas from the reaction between Nd(OBu$^t$)$_3$, Y(OBu$^t$)$_3$, Pr(OBu$^t$)$_3$ and Al(CH$_3$)$_3$ solid products are obtained. In addition, with the methoxides of lanthanides, solid and chemically defined complexes are obtained only with a molar ratio Al/Ln of 4.

The different kinds of complexes which can be obtained in the various cases are better explained by the illustrative examples listed below.

The alkylalkoxy derivatives of the lanthanides of the present invention form a group of products whose existence has not yet been verified in literature.

In fact it is known in scientific and patent literature that alkyl derivatives of lanthanides exist but these are not generally obtained starting from homoleptic salts of lanthanides, such as trichlorides or tricarboxylates, but from bis-cyclopentadienylhalides of lanthanides having general formula Ln(Cp*)$_2$Cl wherein Ln is an element of the group of lanthanides and Cp* is a cyclopentadienyl or pentamethyl-cyclopentadienyl group.

By the reaction of these derivatives with alkyls of lithium or magnesium alkyl derivatives are obtained with the general formula (Cp*)2Ln-R in which alkyl (R) groups and (Cp*) groups are present contemporaneously, which act as stabilizers. It is therefore evident that the preparation of these alkyls requires the use of costly starting products such as bis-cyclopentadienylhalides of lanthanides and lithium and magnesium alkyls.

A detailed documentation on alkyl derivatives of lanthanides of this kind is provided in two lengthy treatises, the first published by G. Wilkinson, G. A. Stone and E. W. Abel "Comprehensive Organometallic Chemistry" Vol. 3, page 173 printed by Pergamon Press in 1982; the second called "Gmelin Handbuch der Anorganische Chemie, Vol. 39-D6 page 208 published by Springer-Verlag in 1983.

The complexes which can be obtained according to the present invention consist instead of alkoxy and alkyl binders linked to lanthanide and aluminium atoms and should therefore be considered mixed alkyl-alkoxy derivatives of lanthanide and aluminium obtained by the reaction of simple and industrially available starting derivatives such as alcoholates of lanthanides and aluminium trialkyls.

The original and innovative character of their synthesis according to the present invention is therefore evident.

The complexes claimed by the Applicant, as well as forming a group of new derivatives which do not result in patent or scientific literature, have proved to be, and this represents a third aspect of the present invention, effective catalysts for the polymerization of olefins and, in particular, diolefins when linked with particular Lewis acids or halogenating agents with or without aluminium alkyls.

Valid but not limiting examples of halogenating agents or Lewis acids can be: aluminium trihalides having the general formula AlX$_3$ with X=Cl, Br, I; monoalkyl dihalides having general formula AlX$_2$R wherein X has the same meaning as above and R is a linear or branched alkyl group containing from 1 to 20 carbon atoms; aluminium monohalidedialkyls having general formula AlXR$_2$ wherein X and R have the same meaning as above; boron halides having general formula BX$_{3-m}$R$_m$ with X and R having the same meaning and m varying from 0 to 3; derivatives of boron having general formula B(C$_6$H$_{5-n}$Y$_n$)$_3$ wherein n can be 0 or between 1 and 5 when Y is fluorine or n is between 1 and 3 when Y is the CF$_3$ group; halogen acids HX with X having the same meaning as above; alkyl halides having general formula RX where R and X have the same meaning as above; silicon halides having the formula SiX$_4$ with X having the same meaning as above; tin halides having the formula SnX$_4$ with X having the same meaning as above.

The activity of the catalysts claimed in the present invention is very high. In particular polymerizations were carried out with concentrations of neodymium complex of less than 5×1$^{-4}$ moles/liter.

The use of such low concentrations of lanthanide complex makes it necessary to use particularly pure solvents or aluminium trialkyls which can improve the efficiency of the catalytic centre.

In addition, as is known in the prior art, in the case of lanthanides, aluminium trialkyls, for example Al(C$_4$H$^i$$_9$)$_3$, or dialkyl-monohydrides, for example AlH(C$_4$H$^i$$_9$)$_2$, can act as molecular weight regulators of the polymer produced.

The polymerizations are carried out by reacting in an aliphatic, cyclo-aliphatic or aromatic hydrocarbon solvent, one of the lanthanide complexes with one of the halogenating agents or Lewis acids mentioned above in the presence of the unsaturated monomer to be polymerized at temperatures ranging from 20° to 100° C., preferably between 0° and 70° C. for the pre-established time.

The final polymer is recovered by pouring the reaction mixture in methanol or ethanol and drying under vacuum. The dried polymer is used for physicochemical determinations such as infrared spectra, differential calorimetric analyses, X-ray analyses, NMR analyses, etc.

Olefinic monomers, for example ethylene, can be used as unsaturated monomers, obtaining in this case linear polymers with a high molecular weight.

Other unsaturated monomers can be those of the diolefinic type, such as butadiene and isoprene, with which high polymers are always obtained with exclusively 1,4 units in the chain but with the possiblity of being able to vary the geometrical stereoregularity of the residuous double bond from 1,4-cis >95% to 1,4-trans >95%. This fact is interesting as these different types of polymer have different characteristics.

The polymer with the highest grade of 1,4-cis units is an elastomer with higher characteristics as shown in the book "Advances in Elastomers and Rubber Elasticity", published by Plenum Publishing Corporation, 1968 page 233.

The polymer with a high grade of 1,4-trans units is on the other hand a highly crystalline polymer with a high boiling point.

Finally, polymers with a varying grade of 1,4-cis and 1,4-trans units are amorphous elastomers if the cis units are statistically distributed, whereas they are thermoelastomeric materials if the 1,4-trans and 1,4-cis units are characterized by blocks.

These differing potentialities of the catalyst family claimed by the applicant are an even further proof of the novelty presented by the applicant if compared to what is claimed in German patent 1812935 wherein ternary systems based on lanthanide alkoxides, aluminium trialkyls and halogenating agents always and only produce high polymers with a very high grade of 1,4-cis. This comparison shows how the behaviour in polymerization of these new complexes claimed herein is not a natural extension of the known art but a completely new and unexpected result.

A description follows, for illustrative but non-limiting purposes, of procedures for the preparation of some of the derivatives which can be obtained according to the present invention as well as their use as catalysts for the polymerization of unsaturated monomers.

The illustrative examples describe the syntheses of the relative complexes starting from Pr $(OBu^t)_3$, $Nd(OCH_3)_3$, $Nd(OBu^n)_3$, $Nd(OBu^t)_3$, $Y(OBu^t)_3$ which are representative for the whole series of metals and alcoholates claimed. For alcoholates such as n-butylates and ter-butylates the value of x in the general formula is 3; with methylates x is 4. Apart from these two values compounds with varying stoichiometries are obtained with analysis values which cannot be referred to definite formulae.

This is a further proof that the compounds claimed represent definite and univocal compounds only for exact reaction ratios between the lanthanide alcoholate and aluminium trialkyl.

EXAMPLE 1

Preparation of the complex $Nd(OCH_3)_3(AlMe_3)_4$.

51 ml of a 1.23 molar solution of $AlMe_3$ (62.4 mmoles) in toluene were added, at 0° C., to a suspension of 3.7 g (15.6 mmoles) of $Nd(OMe)_3$ in 10 ml of toluene. The reaction mixture was left under stirring at 0° C. for 6 hours and the initial suspension was transformed into a only slighty opalescent blue solution.

The solid traces in suspension were separated by filtration and the solvent was removed under vacuum at 0° C. from the resulting limpid solution.

In this way a viscous blue-coloured oil is obtained, which was kept under vacuum, at 0° C., for 20 hours to allow all the volatile substances to be removed. Analyses: found Nd%=26.9; Al%=19.5; $CH_3$=33.5; calculated for $Nd(OCH_3)_3(AlMe_3)_4$: Nd%=27.4; Al%=20.5; $CH_3$%=34.3.

The analysis of the $CH_3$ group was obtained by gas-volumetric analysis decomposing the complex with $H_2O$ dissolved in diglime (dimethylether of diethylene glycol).

The residuous viscous oil was divided into two parts. One part, kept in a refrigerator at −20° C. for several days, solidified into a blue crystalline solid.

All attempts to wash or recrystallize the solid failed owing to its extremely high solubility in all solvents and it therefore had to be used as such. Its IR spectrum proved to be perfectly analogous to that of the oil from which it had derived (FIG. 1).

The second part of the viscous oil was dissolved in hexane and the solution was used for polymerization tests after the titer in neodymium had been analyzed. The concentration of Neodymium proved to be $0.064 \times 10^{-3}$ g Atoms of $Nd/cm^3$.

EXAMPLE 2

Preparation of the complex Nd $(OBu^t)_3(AlMe_3)_3$.

9.1 g (25 mmoles) of $Nd(OBu^t)_3$ in 120 ml of toluene were dissolved in a 250 ml tailed flask.

After cooling the solution to −20° C., 7.4 ml of $AlMe_3$ (76.8 mmoles) dissolved in 30 ml of toluene were added, in about 30 minutes.

The reaction mixture was then kept under stirring at 0° C. for 4 hours, and a slightly turbid blue solution was thus obtained, which was filtered and the solvent removed under vacuum.

The residue was dissolved in 60 ml of pentane and the solution was slowly cooled to −20° C., to obtain the precipitation of a blue crystalline solid which was recovered by filtration at room temperature, dried under vacuum obtaining 6.2 g of solid. The filtrate was concentrated,up to about 30 ml and again cooled to −20° C. obtaining the precipitation of a further 2.5 g of crystalline product for a total yield of 60%.

Analyses: found, Nd=25.1%, Al=14.7% $CH_3$=24.0% Calculated for $Nd(OBu^t)_3(AlMe_3)_3$: Nd=25.1%, al=14.0%, $CH_3$=23.3%. The molecular weight of the compound, measured via cryoscopy in petrol, proved to be 608 against a calculated value of 579.

Figure 2:
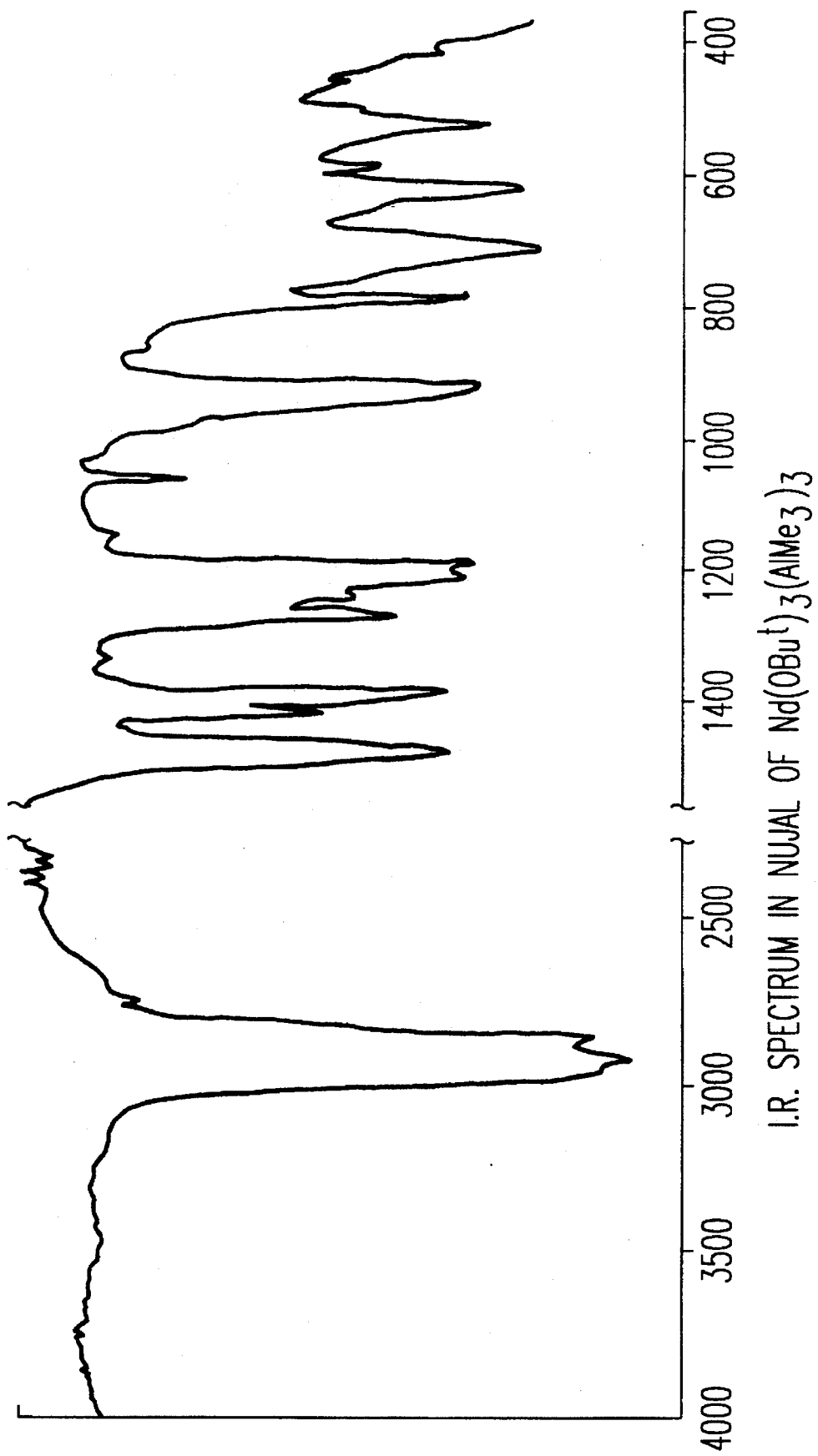
FIG. 2, I.R. Spectrum of Nd(OBu$^t$)$_3$(AlMe$_3$)$_3$.

The IR spectrum of the complex is shown in FIG. 2.

X-ray diffraction measurements on a monocrystal made it possible to establish that the product crystallizes in the rhombohedral system, spacial group P31c, with cell parameters a=16, 226(2) A and c=8, 219(3) A.

EXAMPLE 3–5

Operating with the same procedure described in example 2 the following complexes were obtained: [pr(OBu')(AlMe$_3$)$_3$], [Y(OBu$^t$)$_3$(AlMe$_3$)$_3$] and [Nd(OBu)$_3$(AlMe$_3$)$_3$].

The analytical data of the final products are shown in table 1.

TABLE 1

Analytical data of complexes Ln(OR)$_3$ (AlMe$_3$)$_3$

| Ex. N° | Complex | Color | Analysis Ln(%) | Al(%) | CH$_3$(%) |
|---|---|---|---|---|---|
| 3 | Pr(OBu$^t$)$_3$ (AlMe$_3$)$_3$ | green | 24.5(24.4) | 12.8(14.0) | 24.2(23.4) |
| 4 | Y(OBu$^t$)$_3$ (AlMe$_3$)$_3$ | no color | 16.4(17.0) | 15.9(15.4) | — |
| 5 * | Nd(OBu$^t$)$_3$ (AlMe$_3$)$_3$ | pale blu | 26.5(24.9) | 12.9(14.0) | 22.9(23.3) |

Under brackets we show the calculated values
* = Product isolated as viscous oil

EXAMPLE 6

100 cm of anhydrous hexane and, after cooling to 0° C., 15 g of liquid butadiene using a hypodermic needle directly screwed onto a cylinder containing anhydrous liquid butadiene, are charged into a 200 ml drinking bottle, previously flushed with inert gas and equipped with a magnetic anchor.

The following are added in order to the monomer solution maintained at 0° C.: 0.05×10$^{-3}$ moles of Nd(OCH$_3$)$_3$(AlMe$_3$)$_4$, added as a hexanic solution prepared as described in example 1, and 0.025×10$^{-3}$ moles of AlCl$_3$.

The bottle is then closed with a metallic crown top having a neoprene seal and is placed in a bath thermostat-regulated at 50° C. and equipped with a rotating magnet to ensure that the contents of the bottle are stirred. The polymerization is carried out for an hour and at the end the bottle is opened and the contents discharged into 500 ml of methanol containing 1% of phenolic antioxidant.

The coagulated polymer is dried under vacuum at room temperature for a night and then weighed. 7.8 g (52%) of elastomeric material are obtained, whose structure, analyzed by IR spectrometry, proves to be 96.8% 1,4-cis, 2.7% 1,4-trans and 0.5% 1.2.

Gel PermeationChromatography measurements give Mw=914×10$_3$.

EXAMPLE 7

The polymerization of butadiene is carried out in the presence, together with the lanthanide complex and Lewis acid, of an aluminium alkyl such as, for example, AlH(Bu$^i$)$_2$. Operating as in example 6, 100 cm$^3$ of hexane, 15 g of butadiene, 0.15×10$^{-3}$ moles of AlH(Bu$^t$)$_2$, 0.05×10$^{-3}$ moles of Nd(OMe)$_3$(AlMe$_3$)$_4$, 0.75×10$^{-3}$ moles of AlEtCl$_2$ are introduced in this order.

Polymerization is carried out at 50° C. for 30' and 14.3 g (95%) of dry polymer are obtained with the following characteristics: 1,4-cis=96.2%; 1,4-trans= 3.2%; 1.2=0.6%; Mw=253×10$_3$, Mw/Mn=2.7.

EXAMPLES 8–10

The influence of various Lewis acids on the complex Nd(OMe)$_3$(AlMe$_3$)$_4$ are shown in the polymerization of butadiene.

All the operations were carried out as in example 6. The products used and obtained are shown in table 2.

TABLE 2

| | | Polimerization tests | | | | | | | | |
|---|---|---|---|---|---|---|---|---|---|---|
| | | Lewis acid | Monomer | Time | Convers. | IR Analysis | | | Mw | |
| Ex. N° | Complex | (moles × 10$^{-3}$) | g | hr | % | 1,4-cis | 1,4-trans | 1,2 | ×10$^3$ | Mw/Mn |
| 8 * | Nd(OMe)$_3$(AlMe$_3$)$_4$ | AlMe$_2$Cl(0.1) | 12 | 1.5 | 50 | 97.6 | 1.7 | 0.8 | 929 | 2.2 |
| 9 | " | Bu$^t$Cl(0.05) | 14 | 4.0 | 23 | 69.0 | 29.8 | 1.2 | 258 | 3.9 |
| 10 | " | BCl$_3$(0.012) | 16 | 0.5 | 52 | 97.5 | 2.0 | 0.5 | 606 | 4.8 |

* = For all examples: gAtoms of Nd = 0.05; Monomer = butadiene; Polymerization temperature = 50° C.

EXAMPLES 11–15

The examples show the activity in the polymerization of butadiene of various complexes of lanthanide together with Lewis acids and aluminium trialkyls or dialkylmonohydrides. All the operations were carried out as in example 7. The results are shown in Table 3.

TABLE 3

Polimerization tests with $Ln(OR)_3(AlMe_3)_3$ with Lewis acids and various Aluminium trialkyls

| Ex. n° | Complex moles × 10⁻³ | Lewis acid or halog.agen. (moles × 10⁻³) | AlR₃ moles × 10³ | Monomer g | Time hr | Convers. % | IR Analysis 1,4-cis | IR Analysis 1,4-trans | 1,2 | Mw ×10³ | Mw/Mn |
|---|---|---|---|---|---|---|---|---|---|---|---|
| 11 | Nd(OBu₃)(AlMe₃)₃ 0.05 | AlEtCl₂ 0.075 | AlH(Buⁱ)₂ 0.55 | 15 | 1 | 71 | 96.1 | 2.8 | 1.1 | 40 | 2.6 |
| 12 | Nd(OBu₃)(AlMe₃)₃ 0.05 | B(PhF5)₃ 0.15 | AlH(Buⁱ)₂ 0.55 | 13 | 1 | 88 | 73.0 | 24.5 | 2.5 | 19 | 4.0 |
| 13 | Nd(OBu₃)(AlMe₃)₃ 0.05 | Buᵗ—Cl 0.15 | AlH(Buⁱ)₂ 0.3 | 15 | 4 | 93 | 91.8 | 7.7 | 0.5 | 447 | 3.2 |
| 14 | Pr(OBu)₃(AlMe₃)₃ 0.15 | B(PhF5)₃ 0.15 | AlH(Buⁱ)₂ 1.65 | 17 | 4 | 55 | 0.7 | 96.2 | 3.1 | — | — |
| 15 | Pr(OBu)₃(AlMe₃)₃ 0.15 | AlEtCl₂ 0.23 | AlMe₃ 1.65 | 14 | 1 | 26 | 97.6 | 1.8 | 0.6 | — | — |

EXAMPLES 16–24

The influence is shown of different Lewis acids and aluminium alkyls on the derivative $Nd(OMe)_3(AlMe_3)_4$ in the polymerization of butadiene, operating as described in example 7. The compounds used and the results obtained are shown in table 4.

TABLE 4

Polimerization tests with $Nd(OMe)_3(AlMe_3)_4$ and various Lewis acids or Aluminium trialkyls

| Ex. n° | Complex moles × 10⁻³ | Lewis acid or halog.agen. (moles × 10⁻³) | AlR₃ moles × 10³ | Monomer g | Time hr | Convers. % | IR Analysis 1,4-cis | IR Analysis 1,4-trans | 1,2 | Mw ×10³ | Mw/Mn |
|---|---|---|---|---|---|---|---|---|---|---|---|
| 16 | 0.05 | AlEtCl₂ (0.075) | AlMe₃ (0.55) | 12 | 0.5 | 80 | 98.7 | 1.2 | 0.1 | 956 | 4.4 |
| 17 | " | B(PhF5)₃ (0.15) | AlMe₃ (0.55) | 24 | 0.5 | 81 | 23.7 | 75.1 | 1.2 | 237 | 1.8 |
| 18 | " | BCl₃ (0.05) | AlMe₃ (0.55) | 15 | 0.5 | 84 | 96.8 | 2.7 | 0.5 | 895 | 4.1 |
| 19 | " | Buᵗ—Cl (0.15) | AlH(Buⁱ)₂ (0.30) | 14 | 2.0 | 94 | 87.0 | 12.4 | 0.6 | 324 | 2.4 |
| 20 | " | SnCl₄ (0.04) | AlH(Buⁱ)₂ (0.55) | 15 | 1.0 | 73 | 81.9 | 17.2 | 0.9 | — | — |
| 21 | " | B(PhF5)₃ (0.15) | AlH(Buⁱ)₂ (0.55) | 13 | 1.0 | 91 | 69.5 | 28.0 | 0.9 | 75 | 2.3 |
| 22 | " | Buᵗ—Cl (0.15) | AlH(Buⁱ)₂ (0.15) | 16 | 4.0 | 54 | 94.2 | 5.3 | 0.5 | — | — |
| 23 | " | AlMe₂Cl (0.15) | AlH(Buⁱ)₂ (0.15) | 17 | 0.5 | 87 | 97.4 | 2.0 | 0.6 | 253 | 2.7 |
| 24 | " | AlEtCl₂ (0.075) | AlH(Buⁱ)₂ (0.15) | 13 | 0.5 | 93 | 95.7 | 3.8 | 0.6 | 260 | 2.7 |

We claim:

1. Organometallic complexes of lanthanides, which can be represented by the general formula:

$$Me(OR)_3 * (Me_1 R^1 R^2 R^3)_x;$$

wherein:

Me represents a metal with atomic number 21, or an atomic number between 57 and 71, OR is an alkoxylic group wherein R represents a linear, branched or cyclo-aliphatic alkyl radical containing from 1 to 10 carbon atoms, $Me_1$ represents a metal of the group IIIA, whereas $R^1, R^2, R^3$, can be independently H, or a linear, branched or cyclo-aliphatic alkyl radical containing from 1 to 10 carbon atoms and x is an integer which is 3 or 4.

2. Organometallic complexes of lanthanides according to claim 1, characterized in that Me represents respectively a Neodymium atom (Nd) or a Praseodymium atom (Pr).

3. Organometallic complexes of lanthanides according to claim 1, characterized in that OR is an alkoxylic group wherein R represents a linear, branched or cyclo-aliphatic alkyl radical containing from 1 to 4 carbon atoms.

4. Organometallic complexes of lanthanides according to claim 1, characterized in that OR is an alkoxylic group wherein R represents respectively a methyl, propyl, isopropyl, n-butyl or ter-butyl group.

5. Procedure for the preparation of organometallic complexes of lanthanides having the general formula $$Me(OR)_3 * (Me_1 R^1 R^2 R^3)_x;$$

wherein:

Me represents a metal with atomic number 21, 39, 57–71,

OR is an alkoxylic group wherein R represents a linear, branched or cyclo-aliphatic alkyl radical containing from 1 to 10 carbon atoms, $Me_1$ represents a metal of the group IIIA, whereas $R^1$, $R^2$, $R^3$, can be independently H, or a linear, branched or cyclo-aliphatic alkyl radical containing from 1 to 10 carbon atoms and x is an integer which is 3 or 4, said procedure being characterized in that the alcoholate of the lanthanide $Me(OR)_3$ is dissolved or suspended in a solvent and a solution of aluminium trialkyl is added to the solution/suspension thus obtained in a molar ratio Al/Me of values of between 1 and 4, in the same solvent and at a temperature of between $-30°$ and $+100°$ C., the solution obtained is filtered and the final solution is dried under forced vacuum.

6. Procedure for the preparation of organometallic complexes of lanthanides according to claim 5, characterized in that the addition of the aluminium trialkyl is carried out at a temperature of between $0°$ and $+10°$ C.

7. Procedure for the preparation of organometallic complexes of lanthanides according to claim 5, characterized in that an aliphatic, cyclo-aliphatic or aromatic hydrocarbon is used as solvent.

8. Procedure for the preparation of organometallic complexes of lanthanides according to claim 5, characterized in that the addition of the solution of aluminium trialkyl is carried out under a cap of inert gas within a time range of between 30 and 90 minutes.

9. Process for the preparation of a polymer of an unsaturated monomer, comprising polymerizing the unsaturated monomer with a catalyst comprising an organometallic complex of a lanthanide having the general formula $$Me(OR)_3 * (Me_1 R^1 R^2 R^3)_x;$$

wherein:

Me represents a metal with atomic number 21, 39, 57–71,

OR is an alkoxylic group wherein R represents a linear, branched or cyclo-aliphatic alkyl radical containing from 1 to 10 carbon atoms, Me represents a metal of the group IIIA, $R^1$, $R^2$, $R^3$, can be independently H, or a linear, branched or cyclo-aliphatic alkyl radical containing from 1 to 10 carbon atoms, and x is an integer which is 3 or 4.

10. Polymerization process according to claim 9, characterized in that the stereospecificity of the polymer can vary from about 95% of 1,4-cis to about 95% of 1,4-trans.

* * * * *